United States Patent
Simon et al.

(10) Patent No.: US 7,299,094 B1
(45) Date of Patent: Nov. 20, 2007

(54) SYSTEM AND METHOD FOR IMPLEMENTING AUTOCAPTURE WITHIN BIVENTRICULAR IMPLANTABLE CARDIAC STIMULATION SYSTEMS

(75) Inventors: Scott Patrick Simon, Billings, MT (US); Daniel C. Carlblom, Burnsville, MN (US); John C. Guthrie, Wentzville, MO (US)

(73) Assignee: Pacesetter, Inc., Sylmar, CA (US)

( * ) Notice: Subject to any disclaimer, the term of this patent is extended or adjusted under 35 U.S.C. 154(b) by 653 days.

(21) Appl. No.: 10/354,489

(22) Filed: Jan. 29, 2003

(51) Int. Cl.
*A61N 1/08* (2006.01)

(52) U.S. Cl. .............................. 607/27; 607/9; 607/28
(58) Field of Classification Search ................. 607/27, 607/28
See application file for complete search history.

(56) References Cited

U.S. PATENT DOCUMENTS

| | | | |
|---|---|---|---|
| 5,417,718 A | 5/1995 | Kleks et al. | 607/28 |
| 6,128,535 A * | 10/2000 | Maarse | 607/28 |
| 6,148,234 A | 11/2000 | Struble | 607/28 |
| 6,430,441 B1 | 8/2002 | Levine | 607/28 |
| 6,456,882 B1 | 9/2002 | Schloss | 607/28 |
| 6,937,901 B2 * | 8/2005 | Zhu et al. | 607/27 |
| 2001/0049542 A1 * | 12/2001 | Florio et al. | 607/28 |
| 2001/0049543 A1 | 12/2001 | Kroll | 607/28 |

FOREIGN PATENT DOCUMENTS

| | | |
|---|---|---|
| EP | 1155711 A2 | 11/2001 |
| WO | WO 01/74441 A2 | 10/2001 |
| WO | WO 01/74441 A3 | 10/2001 |

* cited by examiner

*Primary Examiner*—Carl Layno
*Assistant Examiner*—Tammie K. Heller

(57) ABSTRACT

A biventricular pacing system is provided which includes an automatic capture verification system for verifying capture of left ventricular pacing pulses on a beat by beat basis. A loss of capture recovery system delivers a backup safety pulse in the event of loss of capture detected in either the right or left ventricle. An automatic stimulation threshold search system is provided for measuring the capture threshold of both left and right ventricles based on various triggers. An automatic output regulation system for both the left and right ventricular channels is provided to set the pacing amplitude to levels sufficient to ensure capture plus a safety margin. A left ventricular automatic stimulation threshold search is triggered upon detection of any loss of capture in the left ventricle and periodically based on a number of different triggers.

16 Claims, 4 Drawing Sheets

SYSTEM AND METHOD FOR IMPLEMENTING AUTOCAPTURE WITHIN BIVENTRICULAR IMPLANTABLE CARDIAC STIMULATION SYSTEMS

FIELD OF THE INVENTION

The invention generally relates to implantable cardiac stimulation devices, such as pacemakers or implantable cardioverter/defibrillators ("ICDs") and, in particular, to techniques for implementing automatic capture verification and automatic capture threshold detection within biventricular pacing and ICD systems.

BACKGROUND OF THE INVENTION

A pacemaker is a medical device, typically implanted within a patient, which provides electrical stimulation pulses to selected chambers of the heart, i.e., the atrium and/or the ventricle. Such stimulation pulses cause the muscle tissue of the heart (myocardial tissue) to depolarize and contract, thereby causing the heart to beat at a controlled rate. Most pacemakers can be programmed to operate in a demand mode of operation, i.e., to generate and deliver stimulation pulses to the heart only when the heart fails to beat on its own. To this end, the pacemaker senses cardiac activity, i.e., heart beats, and if the heart beats do not occur at a prescribed rate, then stimulation pulses are generated and delivered to an appropriate heart chamber, either the atrium or the ventricle, in order to force the heart to beat.

When operating in a demand mode of operation, the pacemaker defines a period of time, referred to generally as the "escape interval" (which may further be referred to as either an "atrial escape interval" or a "ventricular escape interval," depending upon the mode of operation of the pacemaker) that is slightly longer than the period of time between normal heart beats. Upon sensing such a "natural" (non-stimulated or non-paced) heart beat within the allotted time period, the escape interval is reset, and a new escape interval is started. A stimulation (or pacing) pulse is generated at the conclusion of this new escape interval unless a natural heartbeat is again sensed during the escape interval. In this way, stimulation pulses are generated "on demand," i.e., only when needed to maintain the heart rate at a rate that never drops below the rate set by the escape interval.

The heart rate is monitored by examining the electrical signals that are manifest concurrent with the depolarization or contraction of the myocardial tissue. The contraction of atrial muscle tissue is manifest by the generation of a P-wave. The contraction of ventricular muscle tissue is manifest by the generation of an R-wave (sometimes referred to as the "QRS complex"). The sequence of electrical signals that represent P-waves, followed by R-waves (or QRS complexes) can be sensed from inside of or directly on the heart by using sensing leads implanted inside or on the heart, e.g., pacemaker leads; or by using external electrodes attached to the skin of the patient.

Most modern implantable pacemakers are programmable. That is, the basic escape interval (atrial and/or ventricular) of the pacemaker, as well as the sensitivity (threshold level) of the sensing circuits used in the pacemaker to sense P-waves and/or R-waves, as well as numerous other operating parameters of the pacemaker, may be programmably set at the time of implantation or thereafter to best suit the needs of a particular patient. Hence, the pacemaker can be programmed to yield a desired performance.

The operation of a pacemaker as described above presupposes that a stimulation pulse generated by the pacemaker effectuates capture. As used herein, the term "capture" refers to the ability of a given stimulation pulse generated by a pacemaker to cause depolarization of the myocardium, i.e., to cause the heart muscle to contract, or to cause the heart to "beat." A stimulation pulse that does not capture the heart is thus a stimulation pulse that may just as well have not been generated, for it has not caused the heart to beat. Such a non-capturing stimulation pulse not only represents wasted energy—energy drawn from the limited energy resources (battery) of the pacemaker—but worse still may provide the pacemaker logic circuits with false information. That is, the logic circuits of the pacemaker may presuppose that each stimulation pulse generated by the pacemaker captures the heart. If the stimulation pulse does not capture the heart, then the pacemaker logic circuits control the operation of the pacemaker based on false information, and may thus control the pacemaker in an inappropriate manner. There is thus a critical need for a pacemaker to properly determine whether a given stimulation pulse has effectuated capture. Failure of a pulse to effectuate capture is referred to as a "loss of capture" or LOC.

While there are many factors that influence whether a given stimulation pulse effectuates capture, a principal factor is the energy of the stimulation pulse. The energy of the stimulation pulse, in turn, is determined by the amplitude and width of the stimulation pulse generated by the pacemaker (the "output settings") and the electrical resistance of the pacemaker system/tissue interface circuit. Advantageously, in a programmable pacemaker, both the amplitude and pulse width of the stimulation pulse are parameters that may be programmably controlled or set to a desired value. Typically, over the lifetime of a device, the Pulse Width is left at a fixed value (usually 4 or 5 milliseconds) and the Amplitude (Voltage) is varied to adjust for changing capture requirements.

An implantable pacemaker or ICD derives its operating energy, including the energy to generate a stimulation pulse, from a battery. The energy required to repeatedly generate a stimulation pulse dominates the total energy consumed by a pacemaker. Hence, to the degree that the energy associated with the stimulation pulse can be minimized, the life of the battery can be extended and/or the size and weight of the battery can be reduced. Unfortunately, however, if the energy associated with a stimulation pulse is reduced too far, the stimulation pulse is not able to consistently effectuate capture, and the pacemaker is thus rendered ineffective at performing its intended function. It is thus desirable for a pacemaker to adjust the amplitude of a stimulation pulse to an appropriate level that provides sufficient energy to effectuate capture, but does not expend any significant energy beyond that required to effectuate capture.

Initially, the most common technique used to adjust the stimulation amplitude to an appropriate level was manually, using the programmable features of the pacemaker. That is, at the time of implant, a cardiologist or other physician conducts some preliminary stimulation tests to determine the amplitude a given stimulation pulse must have to effectuate capture at a given tissue location. This stimulation pulse amplitude is hereafter referred to as the "capture threshold." If the preliminary tests indicate that the capture threshold is high (compared to the average patient) then the lead will be repositioned until a "good" threshold is found. Once it has been determined that the thresholds are acceptable, the stimulation electrode is then left in place and the amplitude and/or width of the stimulation pulse is set to a level that is typically 2 to 3 times greater than the amplitude determined in the preliminary tests. The increase in amplitude beyond the measured pacing threshold is considered as a "safety margin."

During the acute phase, e.g., over a period of days or weeks after implant, the capture threshold usually increases significantly over that measured at implant. Hence, having a safety margin factored into the stimulation pulse amplitude allows the stimulation pulses generated by the pacemaker to continue to effectuate capture despite this acute change in the capture threshold. Unfortunately, however, much of the energy associated with the safety margin represents wasted energy, and shortens the life of the battery. Near the end of the acute phase the threshold typically returns back down to a value near the level measured at implant. After the acute phase the lead enters the chronic phase. Typically, during the chronic phase the threshold remains relatively stable compared to the acute phase. If left unchecked, the safety margin determined necessary at implant is extremely wasteful during the chronic phase. Thus, once the lead enters the chronic phase, typically the pacing output level is adjusted lower, but never less than 2-3 times threshold.

Some single-chambered pacemakers (e.g. pacemakers that pace in the left ventricle only) and dual-chambered pacemakers (e.g. pacemakers that pace in both the left ventricle and left atrium) now include an automatic stimulation threshold search system which, following implant of the pacemaker, automatically determines the minimum capture threshold and sets the stimulation pulse amplitude accordingly. The stimulation threshold search system periodically re-determines the threshold and re-sets the stimulation pulse amplitude, if needed. Hence, if the threshold increases with time, the stimulation pulse amplitude is increased as needed to maintain capture. If the threshold decreases with time, the stimulation pulse amplitude is decreased as needed so that energy is not wasted. These automatic features represent an alternative to manual adjustment of threshold. Because the pacing threshold is frequently checked, a smaller safety margin can be used. In dual-chambered pacemakers, the stimulation threshold search system is typically applied only to ventricular pacing pulses.

In the St. Jude Medical Autocapture system, to periodically determine the capture threshold, the "stimulation threshold search" system applies a sequence of stimulation pulses to the heart tissue with differing pulse amplitudes and determines the lowest amplitude sufficient to effectuate capture. Autocapture is a registered trademark of St. Jude Medical, Inc. In the Autocapture system, an "automatic capture verification" system looks for an evoked response following the pulse to determine on a beat by beat basis if capture has been effectuated by a stimulation pulse. If an evoked response is detected, capture is thereby verified. If no evoked response is detected, a backup pulse is delivered and a new stimulation threshold search is performed to determine a new capture threshold. The pulse amplitude is then set to a level just above the threshold, a function termed "Automatic Output Regulation." Herein, the term "Autocapture" is used to refer to systems that provide for beat by beat automatic capture verification with a backup safety pulse and automatic stimulation threshold search with the automatic output regulation.

More specifically, Autocapture provides for:
automatic Capture Verification, which monitors every paced beat for the presence of an evoked response;
automatic Loss of Capture Recovery, which in the absence of an evoked response triggers an automatic backup safety pulse to ensure capture, ensuring patient safety;
automatic stimulation threshold search, which, due to various triggers initiated by the device algorithms, measures pacing thresholds to determine the pulse amplitude requirement; and
Automatic Output Regulation, which sets the pulse amplitude to an "operating amplitude" just above the measured threshold, ensuring the lowest energy level that ensures capture and thus optimizing device longevity.

An example of an Autocapture system is described in detail within U.S. Pat. No. 5,417,718 to Kleks et al., entitled "System for Maintaining Capture in an Implantable Pulse Generator", which is incorporated by reference herein.

Autocapture has proven to be highly successful within single-chambered pacemakers and dual-chambered pacemakers. However, heretofore, Autocapture has not been applied to biventricular pacing devices, i.e. dual-chambered pacemakers that have the capability for delivering synchronized pacing pulses to the left and right ventricles. Biventricular pacemakers have shown the ability to increase the performance of patients with congestive heart failure (CHF) by synchronizing the contraction between the left and right side of the heart. Autocapture has not been employed within biventricular pacing devices, in part, due to the potential for an evoked response from one ventricle, for instance the left ventricle, to create a false positive evoked response signal on the opposite channel—the right ventricular (RV) channel. For example, within a biventricular system providing separate sensing and pacing leads in the left and right ventricles, the portion of the R-wave generated by depolarization of the left ventricle in response to the a Left ventricular (LV) pacing pulse will propagate into the right ventricle where it might be sensed by the RV sensing lead mounted therein. If it is sensed in the right ventricle after a separate pacing pulse is delivered to the right ventricle, the device may misinterpret the sensed signal as being representative of depolarization of the right ventricle triggered by the RV pacing pulse. Hence, even if the amplitude for the RV pacing pulse is below the threshold at which it will evoke a response in the right ventricle, the device will nevertheless assume that the pulse amplitude is sufficient and that the pulse had properly captured the right ventricle. This phenomenon is referred to herein as "cross channel evoked response sensing".

As a result, it does not appear that Autocapture has ever been provided within commercially available biventricular pacing systems. Hence, patients with implantable biventricular pacing devices do not gain the benefits of the Autocapture technique. As noted above, without Autocapture, the amplitude of individual pacing pulses must typically be set to a sufficiently high level to substantially guarantee that each pulse will be captured, thereby consuming a greater amount of energy from the battery of the implantable device and hence diminishing device longevity and requiring more frequent replacement. Energy consumption within a biventricular device is particularly critical in view of the need to deliver pacing pulses to both left and right ventricles and in view of the generally higher pulse amplitudes required within the left ventricle. Also, there is always a risk that pacing pulses will not properly be captured, perhaps because the physiological threshold needed for evoking a response within the heart of the patient has increased with time as a result of disease progression, medication, lead dislodgment, or other factors. Hence, without automatic capture verification, there is a risk that biventricular pacing therapy needed by the patient will not properly be delivered to the patient with potentially serious consequences.

SUMMARY

In accordance with a first embodiment, which primarily pertains to Capture Verification, an implantable cardiac stimulation device is provided with: a biventricular pacing system operative to deliver pacing pulses to the left and right ventricles of the patient and a capture verification system operative to detect LOC of each LV pacing pulse, on a beat by beat basis, during biventricular pacing, and to detect LOC of RV and LV pacing stimuli at the time of threshold tests. Additionally, the biventricular pacing system may include a stimulation threshold search system operative to determine LV and RV pacing pulse amplitudes sufficient to achieve capture and an output regulation system to set the LV and RV amplitudes at a level slightly above capture threshold. The biventricular pacing system controls the stimulation threshold search system to perform LV and RV threshold searches under various circumstances including triggering an LV search upon detection of LOC of an LV pulse.

In accordance with a second embodiment, which primarily pertains to Loss of Capture recovery, an implantable cardiac stimulation device is provided with: a biventricular pacing system; a capture verification system operative to detect LOC of an LV pacing pulse; and a loss of capture recovery system operative to deliver an LV backup pulse upon detection of LOC of an LV pulse on a beat by beat basis. Additionally, the biventricular pacing system may include the aforementioned stimulation threshold search system. If so, LV or RV backup pulses are also preferably provided when needed during stimulation threshold searches.

In accordance with a third embodiment, which primarily pertains to Automatic Output Regulation, an implantable cardiac stimulation device is provided with: a biventricular pacing system; a capture verification system operative to detect LOC of a pacing pulse; and an output regulation system that sets a pacing pulse amplitude to the amplitude sufficient to achieve capture plus a safety margin.

In accordance with a fourth embodiment, which pertains to Capture Verification, Loss of Capture recovery and Automatic Output Regulation, an implantable cardiac stimulation device is provided with: a biventricular pacing system; a capture verification system operative to detect LOC of a pacing pulse; a loss of capture recovery system operative to deliver a backup pulse upon detection of LOC of a pacing pulse; a stimulation threshold search system operative to determine pacing pulse amplitudes sufficient to achieve capture; and an output regulation system that sets a pacing pulse amplitude to the amplitude sufficient to achieve capture as determined by the stimulation threshold search system plus a safety margin.

Hence, in view of the various aspects of the invention, some or all of the features and advantages of Autocapture are advantageously provided within a biventricular system. In an exemplary embodiment, beat by beat capture verification is performed during biventricular pacing on LV pulses but not RV pulses. LV capture verification is provided on beat-by-beat basis and LOC recovery is provided upon each LOC. In addition, an LV stimulation threshold search is triggered upon detection of each LV LOC. The LV search is also triggered upon events including, but not limited to removal of a programming wand or placement of a magnet over the chest of the patient near the implanted device. LV searches are also performed periodically following expiration of an LV search timer. An RV stimulation threshold search is also performed, but only periodically. RV capture verification and LOC recovery are only employed during the RV search and not during routine biventricular pacing. During an LV search, an LV-RV delay value is set to a "non-interference" LV-RV delay value sufficient to ensure that ongoing RV pacing does not interfere with the LV search. Likewise, during an RV search, an RV-LV delay value is set to a "non-interference" RV-LV delay value sufficient to ensure that ongoing LV pacing does not interfere with the RV search. Alternatively, RV pacing is inhibited during the LV search and LV pacing is inhibited during the RV search.

In the exemplary embodiment, by providing automatic stimulation threshold detection for both the left and right ventricles, the pulse amplitudes for both the LV and RV pulses may be set to reduced levels so as to conserve energy and enhance device longevity. In particular, with beat-by-beat capture verification provided for LV pulses, the LV pulse amplitude can be set very close to the LV threshold to thereby achieve maximum energy savings on LV pulses. Although beat-by-beat capture verification is not performed for RV pacing pulses (other than during an RV stimulation threshold search), capture of RV pacing pulses can nevertheless be substantially assured by performing an RV stimulation threshold search periodically and by employing an output regulation system to provide a reasonable safety margin on the RV pulses. As note above, RV capture may be less critical than LV capture in biventricular pacing systems and so the overall biventricular pacing system can afford lower resolution on measuring the RV threshold level.

Thus, the invention provides techniques for implementing the features of Autocapture within biventricular systems to thereby extend the benefits of Autocapture to patients receiving biventricular pacing therapy. Other features and advantages of the invention are described below.

BRIEF DESCRIPTION OF THE DRAWINGS

Further features and advantages of the present invention may be more readily understood by reference to the following description taken in conjunction with the accompanying drawings, in which.

DETAILED DESCRIPTION OF PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
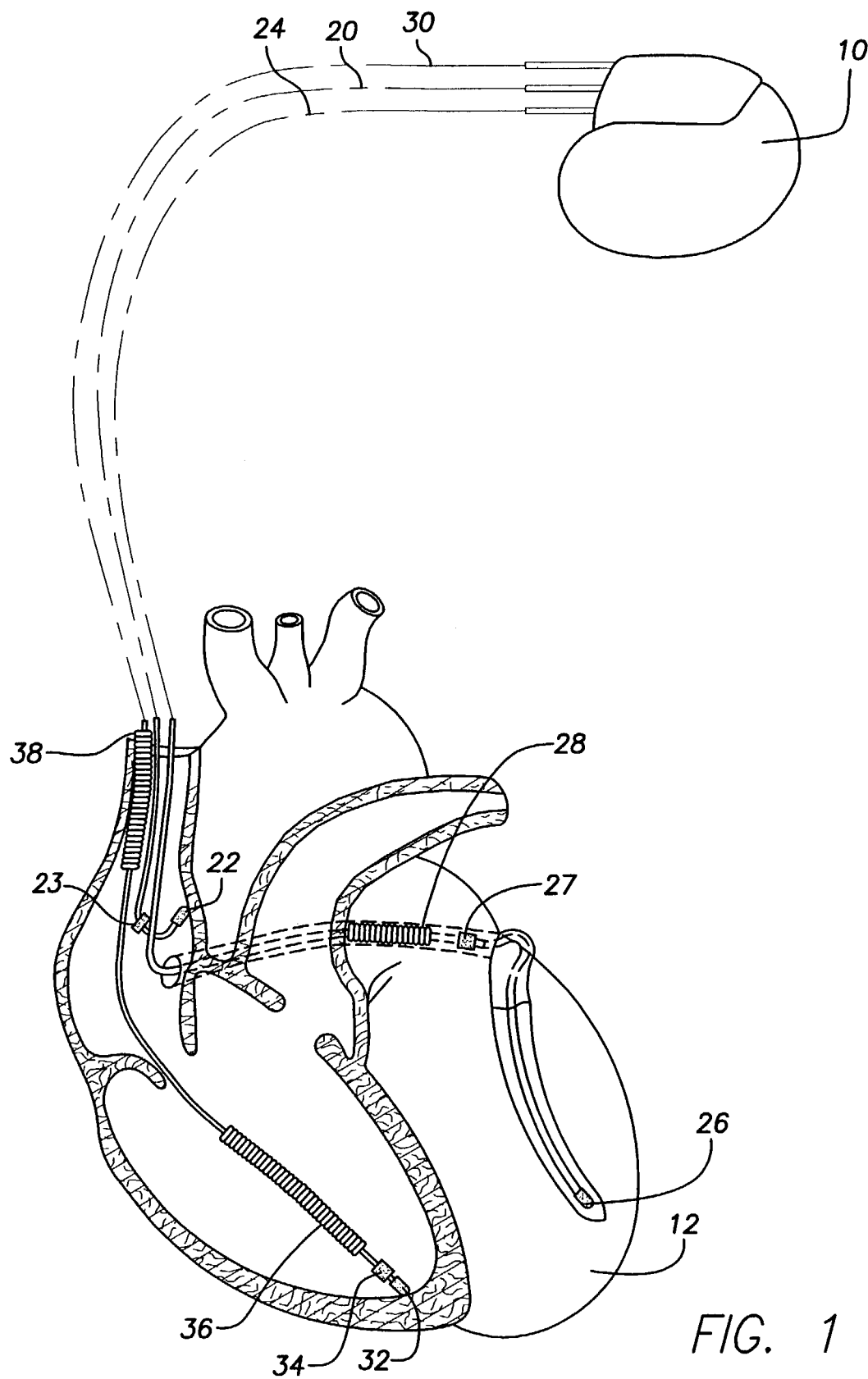
FIG. 1 is a simplified diagram illustrating an implantable stimulation device in electrical communication with at least three leads implanted into the heart of a patient for delivering multi-chamber stimulation and shock therapy and configured in accordance with the invention to perform biventricular pacing.
Figure 2:
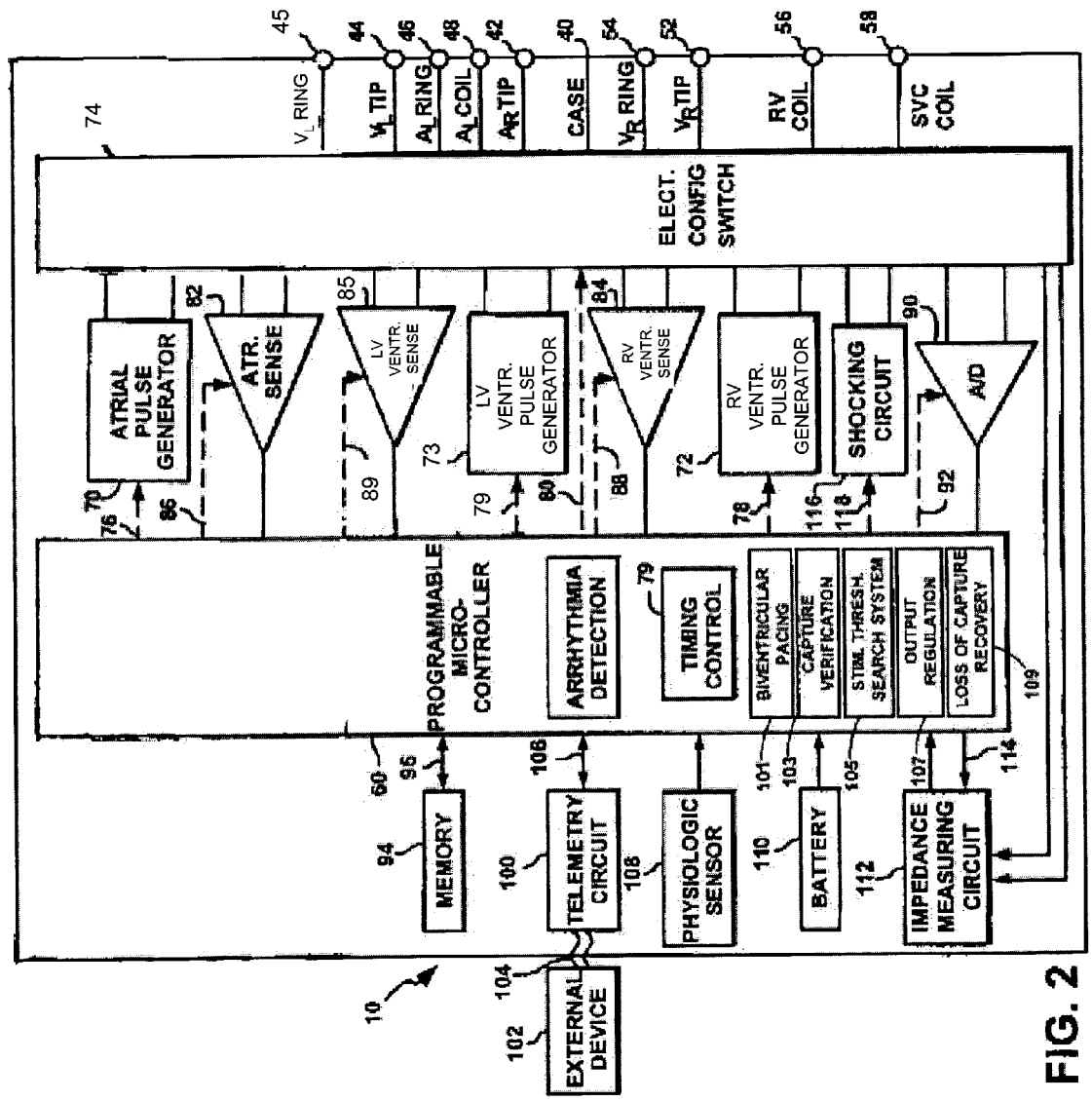
FIG. 2 is a functional block diagram of the implantable cardiac stimulation device of FIG. 1 illustrating basic elements of a stimulation device and particularly illustrating components for controlling biventricular pacing, capture verification, stimulation threshold searches, and backup pulses.

The invention may be implemented using the implantable cardiac stimulation device illustrated in FIGS. 1 and 2. An overview of the stimulation device is provided, followed by a detailed description of the invention.

Implantable Device Overview

In FIG. 1, a simplified block diagram is shown of a dual-chamber implantable stimulation device 10, which is capable of treating both fast and slow arrhythmias with stimulation therapy, including cardioversion, defibrillation, and pacing stimulation. To provide atrial chamber pacing stimulation and sensing, the stimulation device 10 is shown in electrical communication with a patient's heart 12 by way of an implantable unipolar atrial lead 20 having an atrial tip electrode 22 implanted in the patient's atrial appendage. The stimulation device 10 is also in electrical communication with the patient's heart 12 by way of an implantable RV lead 30 having, in this embodiment, a RV tip electrode 32, an RV ring electrode 34, a RV (RV) coil electrode 36, and a superior vena cava (SVC) coil electrode 38. Typically, the ventricular lead 30 is transvenously inserted into the heart 12 so as to place the RV coil electrode 36 in the RV apex, and the SVC coil electrode 38 in the superior vena cava. Accordingly, the ventricular lead 30 is capable of receiving cardiac signals, and delivering stimulation in the form of pacing and shock therapy to the right ventricle. The stimulation device 10 is also in electrical communication with the patient's heart 12 by way of an implantable LV lead 24 having, in this embodiment, an LV tip electrode 26 and an LV ring electrode 27. Typically, the LV lead 24 is transvenously inserted into the Coronary Veins of the heart 12. Accordingly, the LV lead 24 is capable of receiving cardiac signals, and delivering stimulation in the form of pacing and shock therapy to the left ventricle. Additionally, an LV coil may be provided.

While a unipolar Atrial is shown in FIG. 1, it is to be understood that a bipolar lead could alternatively be employed. Also, although three leads are shown in FIG. 1, it should also be understood that fewer or additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing and atrial or ventricular shocking therapy.

In FIG. 2, the housing 40 (shown schematically) for the stimulation device 10 includes a connector (not shown) having an atrial tip terminal 42 adapted for connection to the atrial tip electrode 22 of the atrial lead 20. The connector further includes a RV tip terminal 52, an RV ring terminal 54, an RV shocking terminal 56, and an SVC shocking terminal 58 adapted for connection to the ventricular tip electrode 32, the RV ring electrode 34, the RV coil electrode 36, and the SVC coil electrode 38, respectively. The connector further includes an LV tip terminal 44 and an LV ring terminal 45 for connection to the LV tip electrode 26 and LV ring electrode 27, respectively. The housing 40 (often referred to as the "can", "case" or "case electrode") acts as the return (common) electrode, or anode, for both the atrial tip electrode 22 and the ventricular tip electrode 32 during unipolar sensing and as the return electrode for just the ventricular tip electrode 32 during Combipolar sensing. Housing 40 can also act as the return (common) electrode, or anode, for the RV coil electrode 36, and the SVC coil electrode 38. For convenience, the names of the electrodes are shown next to the terminals.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70, an RV pulse generator 72 and an LV pulse generator 73 generate pacing stimulation pulses for delivery by the atrial lead 20, the RV lead 30, and the LV lead 24, respectively, via a switch bank 74. The pulse generators, 70, 72 and 73 are controlled by the microcontroller 60 via appropriate control signals, 76, 78 and 79, respectively, to trigger or inhibit the stimulation pulses. The microcontroller 60 further includes a timing control unit that controls the operation of the stimulation device timing of such stimulation pulses that is known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, sets the polarity of the stimulation pulses by selectively closing the appropriate combination of switches (not shown) as is known in the art.

An atrial sense amplifier 82, RV sense amplifier 84, and an LV sense amplifier 85 are also coupled to the atrial, RV and LV leads 20, 30, and 24, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity. The switch bank also permits the pacemaker to be set to either bipolar sensing, unipolar sensing or Combipolar sensing. For unipolar sensing, the RV TIP and CASE terminals are connected to the RV sense amplifier for sensing a voltage differential there between and the RA TIP and CASE terminals are connected to the atrial sense amplifier for sensing a voltage differential there between and the LV TIP and CASE terminals are connected to the LV sense amplifier for sensing a voltage differential therebetween. For Bipolar sensing, the RV TIP and RV RING terminals are connected to the RV sense amplifier for sensing a voltage differential there between (or LV TIP and LV ring connected to the LV sense amplifier for LV sensing) and the RA TIP and RA RING terminals are connected to the atrial sense amplifier for sensing a voltage differential there between. For Combipolar sensing, the RV TIP and CASE terminals are likewise connected to the ventricular sense amplifier but the A TIP and V TIP terminals are connected to the atrial sense amplifier for sensing a voltage differential between the tips of the atrial and ventricular leads. The discussion of sensing is not critical to the invention but is included for completeness.

Each sense amplifier, 82, 84, and 85 preferably employs a low energy, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. Each sense amplifier, 82, 84 and 85 also receives control signals from the microprocessor, respectively, along lines 86, 88 and 89. The outputs of the atrial and ventricular sense amplifiers, 82, 84 and 85, are connected to the microcontroller 60 which, in turn, inhibits the atrial, RV and LV pulse generators, 70, 72, and 73, respectively, in a demand fashion whenever cardiac activity is sensed in the respective chambers.

For arrhythmia detection, the invention utilizes the atrial and RV sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, activation of special algorithms such as automatic mode switch or high atrial rate episode logging, anti-tachycardia pacing, cardioversion shocks or defibrillation shocks, also known as "tiered therapy"). An arrhythmia detection unit of the microcontroller oversees arrhythmia detection. A morphology detector, not shown, oversees the analysis of morphology.

Cardiac signals are also applied to the inputs of an analog to digital (A/D) data acquisition system 90. The data acquisition system 90 is configured to acquire intracardiac electrogram signals, convert the raw analog data into a digital signal and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

Additionally, microcontroller 60 includes a biventricular pacing controller 101 for controlling biventricular pacing, a capture verification system 103 for verifying capture of RV and LV pacing pulses, a stimulation threshold search system 105 for determining stimulation thresholds, an output regulation block 107 for setting the RV and LV pacing amplitudes based on the stimulation thresholds, and a loss of capture recovery system 109 for delivering backup safety pulses following an LV LOC during normal pacing and following either an LV or RV LOC during LV and RV threshold searches. The operation of these components will be described in greater detail below. The capture verification system 103 utilizes signals from the RV sense amplifier 84 and LV sense amplifier 85 to determine capture in the RV and LV, respectively.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104. The telemetry circuit is also capable of detecting the placement of a magnet near the chest of the patient in which the device is planted. Alternatively, a separate magnet placement detection device may be provided. In any case, the microcontroller is programmed to respond to the detection of such a magnet by performing certain preprogrammed operations such as, as will be described further below, performing an automatic stimulation threshold search.

In the preferred embodiment, the stimulation device 10 further includes a physiologic sensor 108. Such sensors are commonly called "rate-responsive" sensors. The physiological sensor 108 is used to detect the exercise state of the patient, to which the microcontroller 60 responds by adjusting the rate and AV Delay at which the atrial and ventricular pulse generators, 70,72, and 73 generate stimulation pulses. The type of sensor used is not critical to the invention and is shown only for completeness. The stimulation device additionally includes a battery 110 that provides operating energy to all of the circuits shown in FIG. 2. For the stimulation device 10, which employs shocking therapy, the battery must be capable of operating at low current drains for long periods of time and then be capable of providing high-current pulses (for capacitor charging) when the patient requires a shock pulse (preferably, in excess of 2 A, at voltages above 2 V, for periods of 10 seconds or more). The battery 110 should also have a predictable discharge characteristic so that elective replacement time can be detected. Accordingly, the present invention preferably employs lithium/silver vanadium oxide batteries, as is true for most (if not all) such devices to date though any appropriate power cell may be employed. As further shown in FIG. 2, the invention preferably includes an impedance measuring circuit 112, which is enabled by the microcontroller 60 by a control signal 114. The impedance measuring circuit 112 is not critical to the invention and is shown only for the sake of completeness.

Depending upon the implementation, the device may function as an implantable cardioverter/defibrillator (ICD)

device. That is, if it detects the occurrence of an arrhythmia, it automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5 to 10 Joules) or high energy (11 to 40 Joules), as controlled by the microcontroller 60. Such shocking pulses are applied to the patient's heart through at least two shocking electrodes, as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to 40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The remaining figures include flowcharts illustrating improved techniques for implementing Autocapture function within biventricular pacing systems. In the flow charts, the various steps of the methods are summarized in individual "blocks". Such blocks describe specific actions or decisions that are made or carried out as the method proceeds. The flow charts presented herein provide the basis for a "control program" that may be used by the microcontroller (or equivalent) to effectuate the desired control of the stimulation device. Those skilled in the art may readily write such a control program based on the flow charts and other descriptions presented herein.

Biventricular Pacing with Beat by Beat LV Capture Verification

Figure 3:
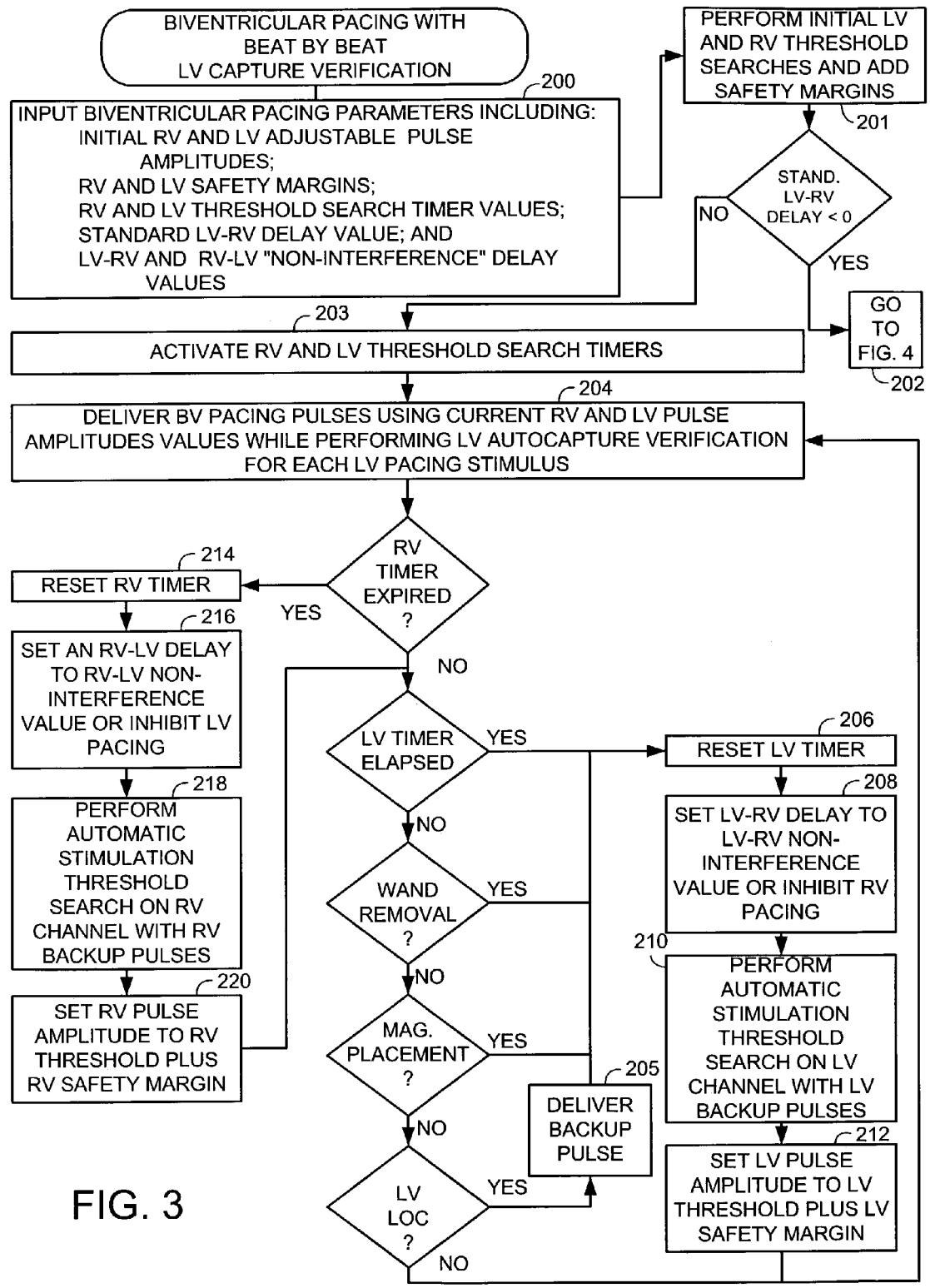
FIG. 3 is a flow chart providing an overview of the operation of an exemplary embodiment of the invention particularly illustrating the manner by which the implantable stimulation device of FIGS. 1 and 2 performs biventricular pacing with beat by beat capture verification of LV pacing pulses, including Loss of Capture Recovery; separate LV and RV stimulation threshold searches; and Output Regulation in both the LV and RV channels.

FIG. 3 illustrates, at a high-level, a technique performed by the Biventricular Autocapture system of the invention (including components 101, 103, 105, 107 and 109 of FIG. 2) for verifying capture of pacing pulses, providing backup pulses, triggering separate left and right stimulation threshold searches, and setting the LV and RV pulse amplitudes.

At step 200, the biventricular pacing controller (101 of FIG. 2) retrieves from memory various parameters for controlling biventricular pacing, LV capture verification, loss of capture recovery, and LV and RV stimulation threshold searches and automatic output regulation. The parameters include initial LV and RV adjustable pulse amplitudes, LV and RV threshold search timer values, LV and RV safety values, a standard LV-RV delay value, and separate RV-LV and LV-RV non-interference delay values.

The LV and RV pulse amplitudes specify initial or default pulse amplitudes to use with the LV and RV pulses. Typically, the LV pulse amplitude is initially set to a value substantially lower than the amplitude that would otherwise be employed without LV capture verification. The lower amplitude is permitted because LV capture verification will be performed and appropriate steps taken in the event LV pulses are not captured. In this manner, overall energy consumption of the stimulation device is reduced thus providing for better battery longevity. With automatic capture verification turned on, the LV pulse amplitude is typically set in the range of 0.5 to 3.0 volts and the RV pulse amplitude is typically in the range of 0.5 to 2.5 volts. As will be explained, these amplitudes are subsequently adjusted following stimulation threshold searches performed by the stimulation threshold search system (105 of FIG. 2.)

The LV and RV search timer values specify how frequently stimulation threshold searches are to be performed to adjust the LV and RV pulse amplitudes. An RV stimulation threshold search is only triggered upon expiration of the RV timer. An LV stimulation threshold search is triggered upon not only expiration of the LV timer but also upon LOC of LV pulses and various other circumstances. The LV and RV safety margin values are adjustable values to be added to the LV and RV pulse amplitudes to help ensure capture.

The LV-RV delay value specifies the time delay between LV and RV pulses to be used during normal biventricular pacing. The LV-RV non-interference delay value is an LV-RV delay value to be used during an LV stimulation threshold search. The LV-RV non-interference delay value is set so as to ensure that ongoing RV pacing does not interfere with the LV stimulation threshold search. The RV-LV non-interference delay value is a timing delay value to be used during an RV stimulation threshold search and is set so as to ensure that ongoing LV pacing does not interfere with the RV stimulation threshold search. Although not shown, other parameters pertinent to biventricular pacing may be retrieved at step 200 as well, such as the durations of various refractory periods. Step 200 only lists parameters particularly pertinent to the techniques of FIG. 3 and is not meant to provide an exhaustive list of all parameters relevant to biventricular pacing.

At step 201, initial LV and RV stimulation threshold searches are performed to adjust the default LV and RV thresholds and safety margins are applied. This is performed using techniques described more fully below. Then, if the standard LV-RV delay is negative, biventricular pacing is activated without beat by beat LV capture verification, at step 202, which is described below in connection with FIG. 4. Assuming, initially, that the standard LV-RV delay is not negative, then processing continues, at step 203, where RV and LV threshold search timers are activated using the LV and RV search timer values, respectively, noted above. These timer values may be set so as to ensure a search is performed at user selected intervals. Beginning at step 204, the biventricular pacing system then begins to deliver biventricular pacing pulses to the left and right ventricles using the initial LV and RV pulse amplitudes and while controlling the capture verification unit (103 of FIG. 2) to verify capture of LV pulses. LV capture verification may be performed generally in accordance with otherwise conventional capture verification techniques but applied to LV pulses during biventricular pacing. Typically, a search window is defined subsequent to the delivery of the pulse during which time the stimulation device seeks to detect the electrical signal representative of the depolarization of the pertinent chamber. If the signal is not detected during the search window, LOC is deemed to have occurred and a backup pulse delivered. Capture verification in the LV is preferably performed on a beat-by-beat basis (i.e. capture verification is performed for each and every beat) but may also be performed on a sampled basis (i.e. capture verification is performed on selected beats, such as every tenth beat).

Additional information regarding techniques for capture verification may be found in: U.S. Pat. No. 5,417,718, also referenced above; U.S. Pat. No. 6,456,882 to Schloss, entitled "Implantable Cardiac Stimulation Device Having Automatic Capture/Threshold Capability Using A Dynamically Adjustable Safety Margin"; and in U.S. Pat. No. 6,430,441 to Levine, entitled "Implantable Cardiac Stimulation Device Having Autocapture/Autothreshold Capability", which are also incorporated by reference herein. In the exemplary embodiment described herein, beat by beat capture of RV pulses is not verified. However, as noted above, RV capture may be less critical than LV capture in biventricular pacing systems and so the overall biventricular pacing system can afford lower resolution on the RV threshold level.

While delivering biventricular pacing at step 204, the biventricular pacing system continuously monitors for various events that, if detected, trigger either an LV or an RV stimulation threshold search. More specifically, if the RV timer expires, an RV stimulation threshold search is triggered. Likewise, if the LV timer expires, an LV stimulation threshold search is triggered. Additionally, an LV stimulation threshold search is performed whenever a telemetry wand is removed from the vicinity of the simulation device to thereby ensure that an LV search is performed following completion of any telemetry operations with the external programmer. A stimulation search is also performed whenever a magnet is placed near the chest of the patient. Assuming that the LV pulse did not result in LOC, that neither the RV or the LV timer has elapsed, and that no wand removal or magnet placement has occurred, the biventricular pacing system continuously performs biventricular pacing at the current RV and LV amplitudes.

If, however, an LV LOC is detected, a backup pulse is delivered, at step 205, by the loss of capture recovery system (109 of FIG. 2). Then, at step 206, the LV timer is reset and, at step 208, the interventricular delay normally used during biventricular pacing is set to the LV-RV non-interference delay value (initially retrieved as step 200.) As noted, the LV-RV non-interference delay is set to a value such that ongoing RV pacing does not interfere with the LV stimulation threshold search. In particular, the LV-RV delay is set so that RV pulses do not interfere with capture verification of LV pulses during the LV search. The LV-RV non-interference delay value is determined in advance during device design and is programmed into the implanted device. The exact value for the LV-RV non-interference delay depends, in part, upon various characteristics of the implanted device and is preferably determined experimentally. In this regard, routine experimentation may be performed during which the LV-RV non-interference delay value is incrementally varied while an LV stimulation search is performed and while RV pacing is on going. The LV-RV non-interference delay value is varied until it reaches a value wherein RV pacing has no adverse effect on the LV stimulation search for all expected ranges of LV stimulation search values. This value for the LV-RV non-interference delay is then programmed into the implanted device. Alternatively, RV pacing is simply inhibited while the LV threshold stimulation search is performed.

At step 210, stimulation threshold search unit (105 of FIG. 2) is activated to perform an LV stimulation threshold search to determine the LV capture threshold. The LV threshold detection search may be performed in accordance with any of a variety of otherwise conventional stimulation threshold search techniques adapted for use with the left ventricle during biventricular pacing. In one example, the LV pulse amplitude is incrementally decreased through some range of values until a LOC of the LV pulse occurs. A backup pulse is delivered following each LV pulses that fails to capture during the search. Then the LV pulse amplitude is increased to again achieve capture. As noted, during the LV search either RV stimulation is inhibited or the LV-RV delay is set such that RV pacing does not interfere with the LV search. More specifically, RV pacing is inhibited so as to ensure that depolarization signals from the right ventricle do not interfere with capture verification of the LV pulses. Alternatively, the LV-RV delay is set long enough so that LV capture can be verified before the RV depolarization is triggered.

One example of a specific capture threshold search technique is described in U.S. patent application Ser. No. 09/716, 642, filed Nov. 20, 2000, entitled "Method And Apparatus For Performing Multiple-Tiered Autocapture Threshold Detection Searches Using An Implantable Cardiac Stimulation Device", which is incorporated by reference herein. This technique may be adapted or modified as needed for use with the present invention.

At step 212, the LV pulse amplitude for biventricular pacing is then set (by the output regulation system 107 of FIG. 2) to the "operating amplitude" which is equal to the LV capture threshold detected by the stimulation threshed search unit plus the programmable LV safety margin value (retrieved in step 200). If the LV threshold search identified an LV threshold that is too high, i.e. above some predetermined upper threshold, the LV pulse amplitude is set to a default "High Output Mode" value. In any case, if RV pacing had been inhibited, it is reactivated. The LV-RV delay is reset to the standard LV-RV delay. Processing returns to step 204 for further biventricular pacing, now using the new value for the LV operating amplitude. By performing an LV threshold search following LOC of an LV pulse, the LV pulse amplitude is thereby automatically adjusted upwardly to a higher value sufficient to ensure continued capture. By periodically performing the LV threshold search (as trigger by the LV timer), the LV pulse amplitude can be adjusted downwardly (when permissible) to thereby achieve energy savings and other advantages.

As noted, an RV threshold search is also performed periodically to reset the RV pulse amplitude to the RV operating amplitude, which is equal to the RV threshold measured by the threshold search plus the programmed RV safety margin. Whenever the RV timer expires, the RV timer is reset, at step 214, and then an RV-LV delay is set, at step 216, equal to the RV-LV non-interference delay value (initially retrieved as step 200.) The RV-LV non-interference delay specifies a time delay from an RV pulse until a subsequent LV pulse and is set to a value such that ongoing LV pacing does not interfere with the RV stimulation threshold search. In other words, during the RV search, the interventricular delay is reversed. If the LV-RV delay is positive during normal biventricular pacing (such that the LV pulse is delivered shortly before the RV pulse), then the pulse order is reversed during the RV search (such that the RV pulse is delivered shortly before the LV pulse.) In any case, as with the LV-RV non-interference delay value, RV-LV non-interference delay value is determined in advance during device design and is programmed into the implanted device. In this regard, the exact value for the RV-LV non-interference delay is experimentally determined via routine experimentation in the same manner as outlined above for the LV-RV non-interference delay. Alternatively, LV pacing is simply inhibited while the RV threshold stimulation search is performed. Moreover, because negative LV-RV delays (RV paced first) and RV only pacing have been shown to be less beneficial to the patient, in an alternative implementation of the RV threshold search, an LV pacing output is triggered as soon as an RV evoked potential is detected or is triggered simultaneous with any RV backup pulse required due to RV loss of capture. This ensures LV depolarization as close as possible to the RV depolarization during the RV threshold search, which may be more beneficial to the patient than simply pacing at the RV-LV non-interference value.

Then, at step 218, the stimulation threshold search unit is activated to perform an RV stimulation threshold search to determine the RV pacing threshold. As with the LV search, the actual RV search may be performed in accordance with otherwise conventional stimulation threshold search techniques adapted for use with the right ventricle during biventricular pacing. In one example, the RV pulse amplitude is incrementally decreased through some range of values until a LOC of the RV pulse occurs, then the RV pulse amplitude is increased enough to again achieve capture. A backup pulse is delivered following any RV LOC during the threshold search. During the RV search, LV pacing is inhibited so as to ensure that depolarization signals from the left ventricle do not interfere with capture verification of the RV pulses. Alternatively, the RV-LV delay is set long enough so that RV capture can be verified before the LV depolarization is triggered. Note that, unlike step 204 wherein RV capture is not verified, RV capture is verified during the RV search of step 218.

At step 220, the RV pulse amplitude is then set (by the output regulation system 107 of FIG. 2) to be equal to the RV operating amplitude, which equals the RV threshold detected by the stimulation threshold search, plus the RV safety margin that was retrieved in step 200. If the RV threshold search identified an RV threshold that is too high, i.e. above some predetermined upper threshold, the RV pulse amplitude is set to the default "High Output Mode" value. In any case, if LV pacing had been inhibited, it is reactivated. The LV-RV delay, if adjusted for the search, is reset to its standard value. Processing returns to step 204 for further biventricular pacing, now using the new value for the RV pulse amplitude. By periodically performing an RV threshold search, the RV pulse amplitude can be lowered when permissible to achieve energy savings and raised when necessary to ensure capture. Although not shown, wand removal and magnet placement may also be used to trigger an RV search.

As noted in connection with step 201, initial LV and RV searches are performed before biventricular pacing is initiated. The initial LV search is performed in the same manner as in steps 208-212. The initial RV search is performed in the same manner as in steps 216-220.

Figure 4:
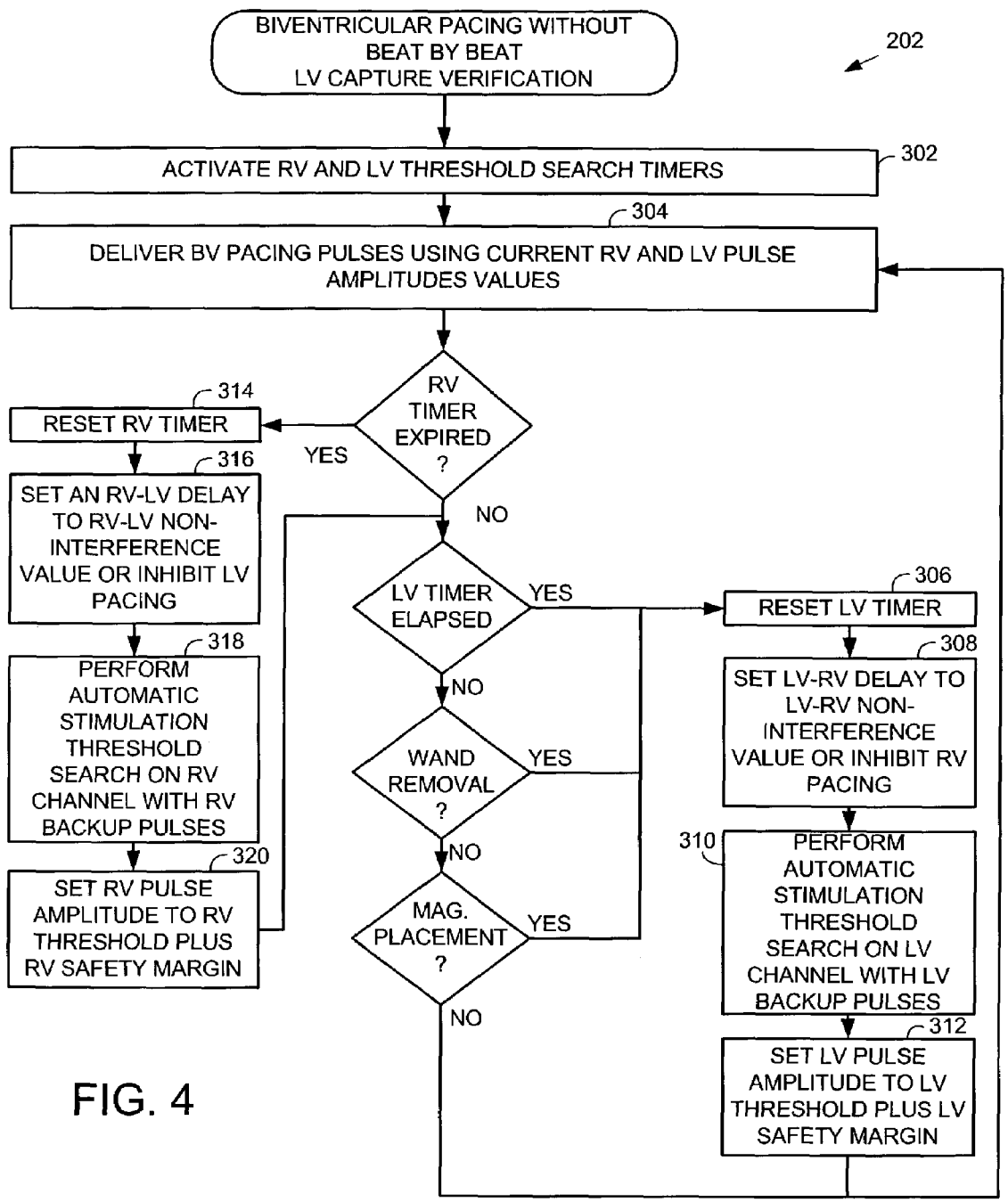
FIG. 4 is a flow chart providing an overview of the manner by which the implantable stimulation device of FIGS. 1 and 2 performs biventricular pacing without beat by beat capture verification for use if an LV-RV delay is programmed to a negative value.

Thus, the technique of the FIG. 3 provides for automatic beat by beat capture verification of LV pacing pulses for use whenever biventricular pacing is performed with a non-negative standard LV-RV delay and which provides for separate LV and RV stimulation threshold searches. With reference to FIG. 4, biventricular pacing without beat by beat LV capture verification is illustrated for use when the standard LV-RV delay is programmed to a negative value. Many of the steps of FIG. 4 are the same as those of FIG. 3 and only pertinent differences will be described in detail. As before, RV and LV threshold search timers are activated, step 302, and, beginning at step 304, the biventricular pacing system begins delivering biventricular pacing pulses. However, unlike the technique of FIG. 3, which provides for beat by beat capture verification of the LV pulses, capture verification is not performed during step 304. While delivering biventricular pacing, the biventricular pacing system continuously monitors for wand removal or magnet placement and for expiration of the LV and RV timers and for any other triggers for threshold searches.

As shown in FIG. 4, expiration of the LV timer, detection of wand removal or magnet placement all trigger an LV threshold search (steps 306-312) performed as described above in connection with steps 206-212 of FIG. 3, except that a larger LV safety margin is employed. Expiration of the RV timer triggers an RV threshold search (steps 314-320) performed as described above in connection with steps 214-220 of FIG. 3. Although not shown, wand removal and magnet placement can additionally trigger RV threshold searches. In any case, so long as the standard LV-RV delay remains negative, biventricular placing continues as shown in FIG. 4.

Thus, various techniques have been described for implementing automatic capture verification (Autocapture) in biventricular pacing devices. The various exemplary techniques described herein overcome the disadvantages discussed above wherein the possibility that an evoked response from one ventricle might cause a false positive evoked response from the other ventricle (i.e. cross channel evoked response sensing) might render conventional automatic capture verification of systems incompatible with biventricular pacing. By enabling automatic capture verification within biventricular pacing systems, biventricular patients benefit from the added safety of automatic capture verification. Additionally, given the increased battery drain created by the second ventricular output combined with the higher pacing thresholds typically required in the left ventricle, electrical current drain savings enabled by automatic voltage regulation may significantly benefit biventricular patients even more so than regular pacer or ICD patients. Furthermore, the beat by beat capture verification with loss of capture recovery may enable maintenance of the hemodynamic benefit of biventricular pacing in the event that the LV capture threshold suddenly rises. Additionally, principles of the invention may be exploited in biatrial systems as well.

The embodiments described herein are merely illustrative of the invention and should not be construed as limiting the scope of the invention, which is to be interpreted in accordance with the claims that follow.

What is claimed is:

1. In an implantable cardiac stimulation device for implant within a patient, a pacing system comprising:
  a biventricular pacing system operative to deliver biventricular pacing pulses to the left and right ventricles of the patient;
  a capture verification system operative to detect a loss of capture of left ventricular (LV) pulses during biventricular pacing;
  a loss of capture recovery system operative to deliver a backup pulse following detection of a loss of capture of an LV pulse; and
  a stimulation threshold search system programmed to determine pacing pulse amplitudes sufficient to achieve capture, wherein the biventricular pacing system is programmed to control the stimulation threshold search system to perform an RV stimulation threshold search while inhibiting LV pacing to prevent LV pacing from interfering with the RV stimulation threshold search.

2. The system of claim 1 wherein the backup pulse is at a maximum energy level.

3. The system of claim 1 wherein the biventricular pacing system controls the stimulation threshold search system to perform an LV stimulation threshold search upon detection of a loss of capture of an LV pulse.

4. The system of claim 3 wherein the biventricular pacing system is further operative to control the stimulation threshold search system to perform an LV stimulation threshold search upon expiration of an LV timer.

5. The system of claim 3 wherein the biventricular pacing system is further operative to control the stimulation threshold search system to perform an LV stimulation threshold search upon detection of removal of a programming wand from the vicinity of the implanted device.

6. The system of claim 3 wherein the biventricular pacing system is further operative to control the stimulation threshold search system to perform an LV stimulation threshold search upon detection of placement of a magnet over the chest of the patient near the implanted device.

7. The system of claim 3 wherein the biventricular pacing system is further operative to control the stimulation threshold search system to perform the LV stimulation threshold search while applying an LV-RV delay sufficient to prevent RV pacing from interfering with the LV stimulation threshold search.

8. The system of claim 3 wherein the biventricular pacing system is further operative to control the stimulation threshold search system to perform the LV stimulation threshold search while inhibiting RV pacing to prevent RV pacing from interfering with the LV stimulation threshold search.

9. The system of claim 3 wherein the biventricular pacing system also comprises an output regulation system operative to set an LV pulse amplitude to an operating LV pulse amplitude sufficient to ensure capture in the left ventricle as determined by the stimulation threshold search system plus an LV safety margin.

10. The system of claim 3 wherein the biventricular pacing system additionally comprises a loss of capture recovery system operative to deliver a backup pulse following detection of a loss of capture of an LV pulse during the stimulation threshold search.

11. The system of claim 3 wherein the biventricular pacing system is further operative to control the stimulation threshold search system to perform the RV stimulation threshold search upon expiration of an RV timer.

12. The system of claim 11 wherein the biventricular pacing system additionally comprises an output regulation system operative to set an RV pulse amplitude to an operating RV pulse amplitude sufficient to ensure capture in the right ventricle as determined by the stimulation threshold search system plus an RV safety margin.

13. The system of claim 11 wherein the biventricular pacing system additionally comprises a loss of capture recovery system operative to deliver a backup pulse following detection of a loss of capture of an RV pulse during the stimulation threshold search.

14. In an implantable cardiac stimulation device for implant within a patient, a pacing system comprising:
  a biventricular pacing system operative to deliver biventricular pacing pulses to the left and right ventricles of the patient;
  a capture verification system operative to detect a loss of capture of left ventricular (LV) pulses during biventricular pacing;
  a loss of capture recovery system operative to deliver a backup pulse following detection of a loss of capture of an LV pulse;
  a stimulation threshold search system programmed to determine pacing pulse amplitudes sufficient to achieve capture in the left or right ventricle upon expiration of a corresponding left or right ventricular timer, wherein the biventricular pacing system is programmed to control the stimulation threshold search system to perform the stimulation threshold search while applying a V-V delay sufficient to prevent pacing in the opposite ventricle from interfering with the stimulation threshold search.

15. The system of claim 14 wherein the biventricular pacing system is further operative to control the stimulation threshold search system to perform an RV stimulation threshold search while inhibiting LV pacing to prevent LV pacing from interfering with the RV stimulation threshold search.

16. In an implantable cardiac stimulation device for implant within a patient, a pacing system comprising:
  a biventricular pacing system operative to deliver biventricular pacing pulses to the left and right ventricles of the patient;
  a capture verification system operative to detect a loss of capture of left ventricular (LV) pulses during biventricular pacing; and
  a loss of capture recovery system operative to deliver a backup pulse following detection of a loss of capture of an LV pulse, wherein the biventricular pacing system employs a programmable LV-RV delay and wherein the biventricular pacing system is programmed to enable the capture verification system whenever the LV-RV delay is not negative and to disable the capture verification system otherwise.

* * * * *